(12) United States Patent
Wang

(10) Patent No.: US 8,637,541 B2
(45) Date of Patent: Jan. 28, 2014

(54) INDOLE DERIVATIVES AS CRTH2 RECEPTOR ANTAGONISTS

(75) Inventor: Zhaoyin Wang, Kirkland (CA)

(73) Assignee: Merck Canada Inc., Quebec (CA)

(*) Notice: Subject to any disclaimer, the term of this patent is extended or adjusted under 35 U.S.C. 154(b) by 335 days.

(21) Appl. No.: 13/120,076

(22) PCT Filed: Sep. 17, 2009

(86) PCT No.: PCT/CA2009/001320
§ 371 (c)(1),
(2), (4) Date: Mar. 21, 2011

(87) PCT Pub. No.: WO2010/031182
PCT Pub. Date: Mar. 25, 2010

(65) Prior Publication Data
US 2011/0201641 A1 Aug. 18, 2011

Related U.S. Application Data

(60) Provisional application No. 61/192,786, filed on Sep. 22, 2008, provisional application No. 61/109,263, filed on Oct. 29, 2008.

(51) Int. Cl.
*A61K 31/437* (2006.01)
*C07D 487/04* (2006.01)

(52) U.S. Cl.
USPC .......................... 514/294; 546/94

(58) Field of Classification Search
USPC ........................... 546/94; 514/294
See application file for complete search history.

(56) References Cited

U.S. PATENT DOCUMENTS

| 7,696,222 B2 | 4/2010 | Wang |
| 2011/0172263 A1 | 7/2011 | Colucci et al. |
| 2011/0178115 A1 | 7/2011 | Leblanc et al. |

FOREIGN PATENT DOCUMENTS

| EP | 1505061 A1 | 2/2005 |
| WO | 2005/040114 A1 | 5/2005 |
| WO | 2007/019675 A1 | 2/2007 |

OTHER PUBLICATIONS

Valentova Jindra et al, Caplus English Abstract, "Chiral Switch" 2004, 53(6).*
Stearns, et al., "Novel Tricyclic Antagonists of the Prostaglandin D2 Receptor DP2 with Efficacy in a Murine Model of Allergic Rhinitis," Bioorganic & Medicinal Chemistry Letters (2009), vol. 19, No. 16, pp. 4647-4651.
Lee, et al., "An Enantioselective 1,2-Aziridinornitosene Synthesis via a Chemoselective Carbon-Hydrogen Insertion Reaction of a Metal Carbene," Journal of Organic Chemistry (1999), vol. 64, No. 12, pp. 4224-4225.
Shichijo, et al., "Chemoattractant Receptor-Homologous Molecule Expressed on TH2 Cells Activation in Vivo Increases Blood . . . ", Journal of Pharmacology (2003), vol. 307, No. 2, pp. 518-525.
Chevalier, et al., "Cutting Edge: Chemoattractant Receptor-Homologous Molecule Expressed on TH2 Cells Plays a Restricting Role on IL-5 . . . ", Journal of Immunology (2005), vol. 175, No. 4, pp. 2056-2060.
Ulven, et al., "Minor Structural Modifications Convert the Dual TP/CRTH2 Antagonist Ramatroban into a Highly Selective . . . ", Journal of Medicinal Chemistry (Feb. 24, 2005), vol. 48, No. 4, pp. 897-900.
International Preliminary Report on Patentability for PCT/CA2009/001320, issued Mar. 22, 2011.
Valentova, J. et al., "Chiral Switch", Ces. slov. Farm., 2004, vol. 53, pp. 285-293.

* cited by examiner

*Primary Examiner* — Rita Desai
(74) *Attorney, Agent, or Firm* — Eric A. Meads; Valerie J. Camara

(57) ABSTRACT

The compound (+) {7R-[[(4-fluorophenyl)sulfonyl] (methyl) ammo]-6,7,8,9-tetrahydropyrido[1,2-a]mdol-10-yl}acetic acid and pharmaceutically acceptable salts thereof are antagonists of the PGD2 receptor, CRTH2, and as such are useful in the treatment and/or prevention of CRTH2-meidated diseases such as asthma.

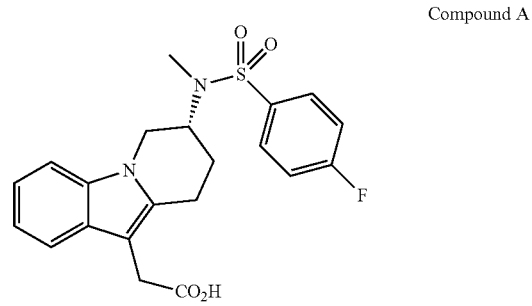

Compound A

2 Claims, No Drawings

INDOLE DERIVATIVES AS CRTH2 RECEPTOR ANTAGONISTS

BACKGROUND OF THE INVENTION

Prostaglandin $D_2$ ($PGD_2$) is a cyclooxygenase metabolite of arachidonic acid. It is released from mast and TH2 cells in response to an immunological challenge, and has been implicated in playing a role in different physiological events such as sleep and allergic responses.

Receptors for $PGD_2$ include the "DP" receptor, the chemoattractant receptor-homologous molecule expressed on TH2 cells ("CRTH2"), and the "FP" receptor. These receptors are G-protein coupled receptors activated by $PGD_2$. The CRTH2 receptor and its expression on different cells including human T-helper cells, basophils, and eosinophils are described in Abe, et al., *Gene* 227:71-77, 1999, Nagata, et al., *FEBS Letters* 459:195-199, 1999, and Nagata, et al., *The Journal of Immunology* 162:1278-1286, 1999, describe CRTH2 receptor. Hirai, et al., *J. Exp. Med.* 193:255-261, 2001, indicates that CRTH2 is a receptor for $PGD_2$.

WO2007019675 discloses CRTH2 antagonists of the formula:

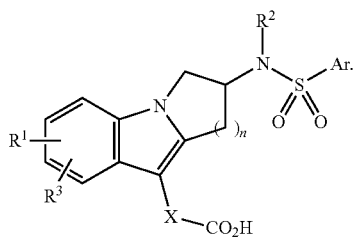

SUMMARY OF THE INVENTION

The present invention provides a CRTH2 receptor antagonist useful for the treatment of various prostaglandin-mediated diseases and disorders; accordingly the present invention provides a method for the treatment of prostaglandin-mediated diseases using the novel compound described herein, as well as pharmaceutical compositions containing it.

DETAILED DESCRIPTION OF THE INVENTION

The present invention relates to Compound A, which is (+){7R-[[(4-fluorophenyl)sulfonyl](methyl)amino]-6,7,8,9-tetrahydropyrido[1,2-a]indol-10-yl}acetic acid or a pharmaceutically acceptable salt thereof. Compound A has the structural formula as shown below:

Compound A

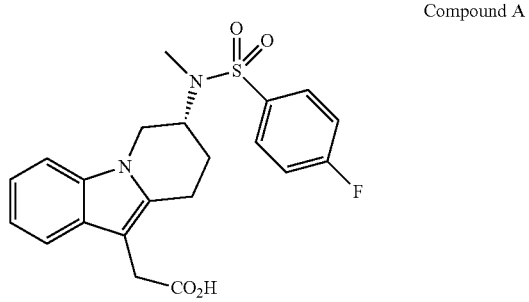 [SMILES: CN([C@@H]1CCc2c(CC(=O)O)c3ccccc3n2C1)S(=O)(=O)c1ccc(F)cc1]

As used herein, the following terms have the indicated meanings. "Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound A and pharmaceutically acceptable excipients.

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. It will be understood that any reference to compound A herein, unless otherwise specified or indicated by context to the contrary, includes pharmaceutically acceptable salts of compound A.

Compound A and pharmaceutically acceptable salts thereof may exist as amorphous or crystalline forms. Some of the crystalline forms for compounds of the present invention may exist as polymorphs and as such all forms are intended to be included in the present invention. In addition, compound A and pharmaceutically acceptable salts thereof may form solvates with water (hydrates) or common organic solvents. Such solvates are encompassed within the scope of this invention.

Utilities

The ability of compound A to interact with prostaglandin receptors makes it useful for preventing or reversing undesirable symptoms caused by prostaglandins in a mammalian, especially human subject. This mimicking or antagonism of the actions of prostaglandins indicates that the compound and pharmaceutical compositions thereof are useful to treat, prevent, or ameliorate in mammals and especially in humans: respiratory conditions, allergic conditions, pain, inflammatory conditions, mucus secretion disorders, bone disorders, sleep disorders, fertility disorders, blood coagulation disorders, trouble of the vision as well as immune and autoimmune diseases. In addition, such a compound may inhibit cellular neoplastic transformations and metastic tumor growth and hence can be used in the treatment of cancer. Compound A may also be of use in the treatment and/or prevention prostaglandin-mediated proliferation disorders such as may occur in diabetic retinopathy and tumor angiogenesis. Compound A may also inhibit prostanoid-induced smooth muscle contraction by antagonizing contractile prostanoids or mimicking relaxing prostanoids and hence may be used in the treatment of dysmenorrhea, premature labor and eosinophil related disorders. More particularly compound A is an antagonist of prostaglandin D2 receptor, CRTH2.

Accordingly, another aspect of the invention provides a method of treating or preventing a prostaglandin mediated disease comprising administering to a mammalian patient in need of such treatment compound A in an amount which is effective for treating or preventing said prostaglandin mediated disease. Prostaglandin mediated diseases include, but are not limited to, allergic rhinitis, nasal congestion, rhinorrhea, perennial rhinitis, nasal inflammation, asthma including allergic asthma, chronic obstructive pulmonary diseases and other forms of lung inflammation; other allergies and allergic reactions such as urticaria, contact dermatitis and allergic conjunctivitis; sleep disorders and sleep-wake cycle disorders; prostanoid-induced smooth muscle contraction associated with dysmenorrhea and premature labor; eosinophil related disorders; thrombosis; glaucoma and vision disorders; occlusive vascular diseases; congestive heart failure; diseases or conditions requiring a treatment of anti-coagulation such as post-injury or post surgery treatment; inflammation; gangrene; Raynaud's disease; mucus secretion disorders including cytoprotection; pain and migraine; diseases requiring control of bone formation and resorption such as for example osteoporosis; shock; thermal regulation including fever; and immune disorders or conditions in which immunoregulation is desirable. More particularly, the disease to be treated is one mediated by prostaglandin D2 such as nasal congestion, pulmonary congestion, and asthma including allergic asthma.

In one embodiment of the invention is a method of treating or preventing a prostaglandin mediated disease comprising administering to a mammalian patient in need of such treatment compound A in an amount which is effective for treating or preventing a prostaglandin mediated disease, wherein the prostaglandin mediated disease is nasal congestion, rhinitis including allergic and perennial rhinitis, and asthma including allergic asthma.

In another embodiment of the present invention is a method of treating or preventing a prostaglandin D2-mediated disease comprising administering to a mammalian patient in need of such treatment compound A in an amount which is effective for treating or preventing a prostaglandin D2 mediated disease wherein said prostaglandin D2 mediated disease is nasal congestion or asthma.

In another embodiment of the present invention is a method for the treatment of nasal congestion in a patient in need of such treatment which comprises administering to said patient a therapeutically effective amount of compound A.

In yet another embodiment of the present invention is a method for the treatment of asthma, including allergic asthma, in a patient in need of such treatment which comprises administering to said patient a therapeutically effective amount of compound A.

Dose Ranges

The magnitude of prophylactic or therapeutic dose of compound A will, of course, vary with the nature and the severity of the condition to be treated and the route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising compound A with a pharmaceutically acceptable carrier. For the treatment of any of the prostanoid mediated diseases compound A may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256, 108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium.

For this purpose any bland fixed oil may be employed including synthetic mono- or diglycerides. In addition, fatty acids such as oleic acid find use in the preparation of injectables.

Compound A may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing compound A are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of prostaglandin mediated diseases, compound A may be co-administered with other therapeutic agents. Thus in another aspect the present invention provides pharmaceutical compositions for treating prostaglandin mediated diseases comprising a therapeutically effective amount of compound A and one or more other therapeutic agents. Suitable therapeutic agents for combination therapy with compound A include: (1) a DP receptor antagonist such as S-5751; (2) a corticosteroid such as triamcinolone acetonide; (3) a β-agonist such as salmeterol, formoterol, terbutaline, metaproterenol, albuterol and the like; (4) a leukotriene modifier, including a leukotriene receptor antagonist such as montelukast, zafirlukast, pranlukast, or a lipooxygenase inhibitor including 5-lipooxygenase inhibitors and FLAP (5-lipooxygenase activating protein) inhibitors such as zileuton; (5) an antihistamine such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (6) a decongestant including phenylephrine, phenylpropanolamine, pseudophedrine, oxymetazoline, ephinephrine, naphazoline, xylometazoline, propylhexedrine, or levo-desoxyephedrine; (7) an antiitussive including codeine, hydrocodone, caramiphen, carbetapentane, or dextramethorphan; (8) another prostaglandin ligand including prostaglandin F agonist such as latanoprost;

misoprostol, enprostil, rioprostil, ornoprostol or rosaprostol; (9) a diuretic; (10) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (11) cyclooxygenase-2 (COX-2) inhibitors such as celecoxib and rofecoxib; (12) inhibitors of phosphodiesterase type IV (PDE-IV) e.g. Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-1a, interferon beta-1b); (17) anticholinergic agents such as muscarinic antagonists (ipratropium bromide and tiotropium bromide), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2) antagonists such as FK-3657, TP receptor antagonists such as seratrodast, neurokinin antagonists (NK1/NK2), VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206. In addition, the invention encompasses a method of treating prostaglandin $D_2$ mediated diseases comprising: administration to a patient in need of such treatment a non-toxic therapeutically effective amount of compound A, optionally co-administered with one or more of such ingredients as listed immediately above.

Methods of Synthesis of Compound A:

Compound A can be prepared according to the procedures of the following Schemes and Examples, using appropriate materials and are further exemplified by the following specific examples. The compounds illustrated in the examples are not, however, to be construed as forming the only genus that is considered as the invention. The Examples further illustrate details for the preparation of the compounds of the present invention. Those skilled in the art will readily understand that known variations of protecting groups, of reagents, as well as of the conditions and processes of the following preparative procedures, can be used to prepare these compounds. It is also understood that whenever a chemical reagent such as an isocyanate, a boronic acid, or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI).

List of Abbreviations:

Alk=alkyl; APCI=atmospheric pressure chemical ionization; Ar=aryl; ATA-117=Amine-Transaminase-117; Boc=tert-butoxycarbonyl; $CH_2Cl_2$=dichloro methane; br=broad; Cbz=benzyloxycarbonyl; d=doublet; DIPEA=N,N-diisopropylethylamine; DMAP=4-dimethylaminopyridine; DMF=N,N-dimethylformamide; DMSO=dimethylsulfoxide; ESI=electrospray ionization; EtOAc=ethyl acetate; $Et_2O$=ethyl ether; FDH=formate dehydrogenase; h=hour(s); Hex=hexanes; HOAc=acetic acid; KOH=potassium hydroxide; LC-MS=liquid chromatography-mass spectroscopy; LDH=lactate dehydrogenase; LiOH=lithium hydroxide; m=multiplet; MeOH=methyl alcohol; min=minutes; $MgSO_4$=magnesium sulfate; $MnO_2$=manganese oxide; MS=mass spectroscopy; MTBE=methyl tert-butyl ether; $NaBH_4$=sodium borohydride; $Na_2SO_4$=sodium sulfate; $Na_2S_2O_3$=sodium thiosulphate; NAD=nicotinamide Adenine dinucleotide; NaH=sodium hydride; $NaHCO_3$=sodium bicarbonate; $NH_4Cl$=ammonium chloride; $NH_4OAc$=ammonium acetate; NMR=nuclear magnetic resonance spectroscopy; NMM=N-methyl morpholine; PG=protecting group; PPTS=pyridinium para-toluenesulfonate; rt=room temperature; s=singlet; t=triplet; $SOCl_2$=thionyl chloride; TBAF=tetrabutyl ammonium fluoride; TBSCl=tert-butyldimethylsilyl chloride; THF=tetrahydrofuran; TFA=trifluoroacetic acid; TLC=thin-layer chromatography; TMSCl=chlorotrimethyl silane; TsCl=p-toluenesulfonyl chloride.

Method A (Scheme 1): Commercially available ethyl indole-2-carboxylate 1 is converted to indole-2-carboxaldehyde 2 by treatment with $LiAlH_4$ followed by oxydation with $MnO_2$. Wittig reaction of 2 with a phosphorane such as ethyl (triphenylphosphoranylidene)acetate provides α,β-unsaturated ester 3, which is alkylated with t-butyl bromoacetate and a base such as cesium carbonate to give the diester 4. Hydrogenation of 4 yields the corresponding diester 5. Treatment of 5 with a base such as potassium tert-butoxide gives the cyclic β-ketoester 6. Decarboxylation of 6 can be affected by refluxing in toluene in the presence of silica gel to give the tricyclic ketone 7. Reduction of ketone 7 with $NaBH_4$ affords alcohol 8 which can be converted to azide 9 by mesylation followed by displacement with sodium azide. Reduction of 9 under hydrogenation conditions provides the corresponding amine 10. Treatment of this amine with 4-fluorophenyl sulfonyl chloride in the presence of a base such as triethylamine affords the aryl sulfonamide 11. The latter can be N-methylated by treatment with a base such as sodium hydride followed by methyl iodide to give the N-methyl aryl sulfonamide 12. Reaction of 12 with oxalyl chloride followed by esterification with methanol yields the α-keto ester 13. Reduction of ketone group in 13 with $NaBH_4$ gives the corresponding α-hydroxy ester 14. Deoxygenation of 14 can be achieved by treatment with $Et_3SiH$ in TFA or alternatively by reaction with TMSCl and sodium iodide in acetonitrile to give the corresponding indole acetic ester 15. Racemic 15 can be resolved into two pure enantiomers by chiral HPLC separation and subsequent hydrolysis of the enantiomer with the R configuration in aqueous base yields the final enantiomerically pure 16.

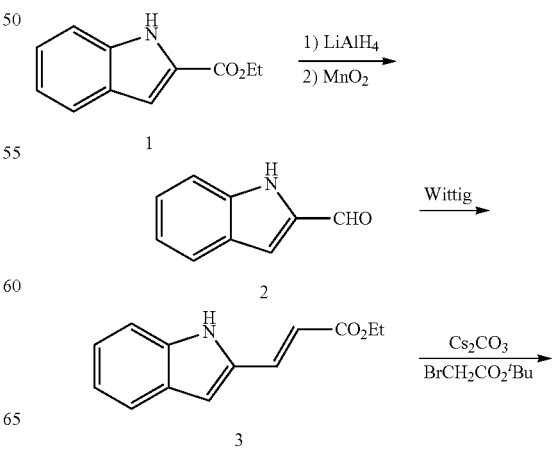

SCHEME 1

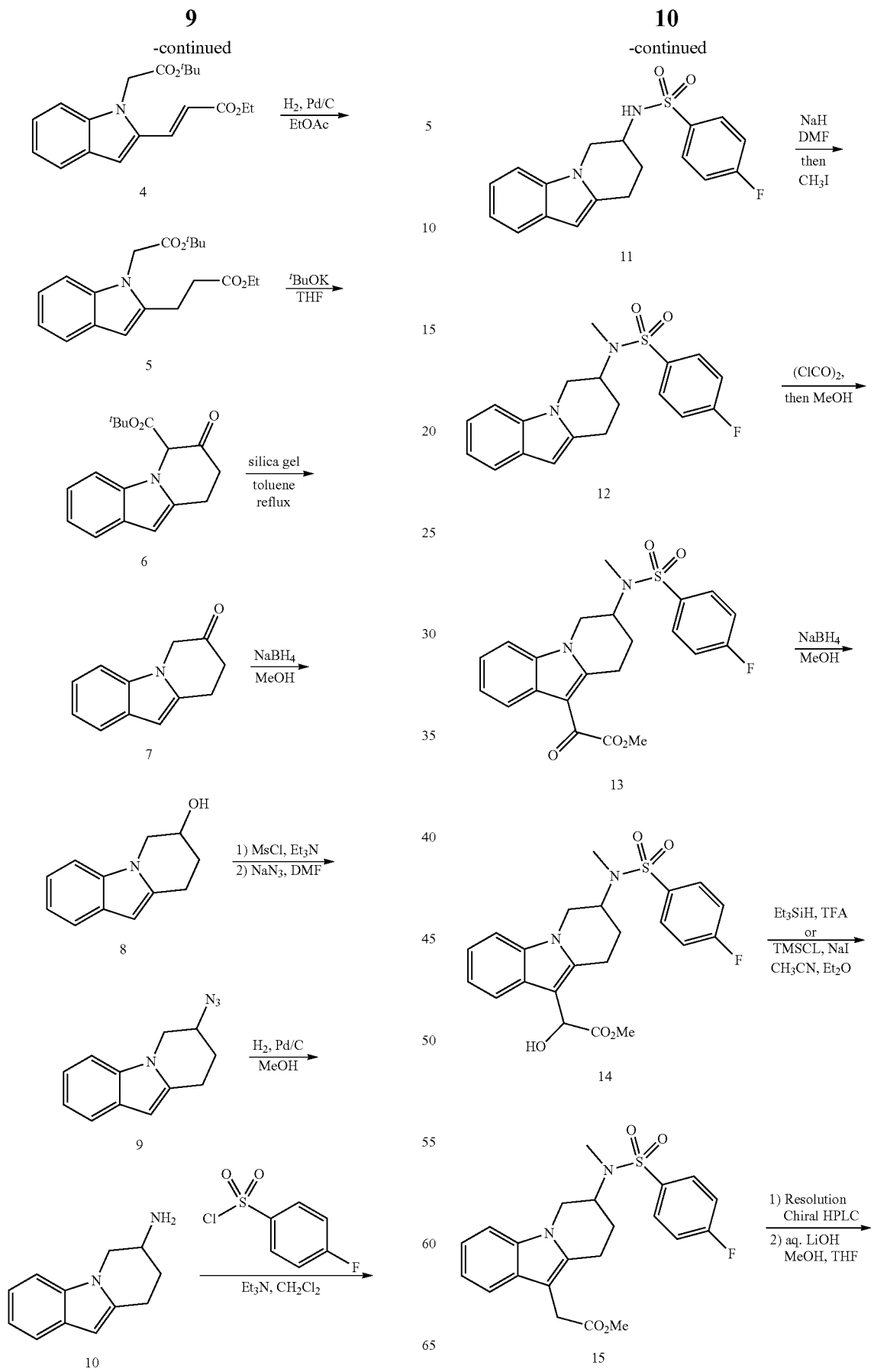

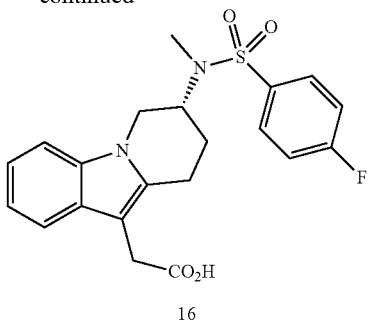

N-methyl morpholine followed by treatment with excess diazomethane give the corresponding diazomethylketone 20. Rhodium catalyzed carbene insertion of diazoketone 20 yields the tricyclic ketone 21. Conversion of 21 into chiral amine 22 can be accomplished enzymatically using a transaminase supplied with an amino acid such as Alanine, cofactors and coupled with a dehydrogenase catalytic system. Coupling of chiral amine 22 with 4-fluorobenzenesulfonyl chloride in the presence of a base gives the sulfonamide 23. N-methylation of 23 is accomplished with methyl iodide in conjunction with a base such as sodium hydride or $Cs_2CO_3$ and provides 24. Hydrolysis of the ester 24 in aqueous base yields the desired chiral acid 16.

Method B (Scheme 2):

Resolution of the racemic sulfonamide 12 using standard chiral HPLC techniques affords the enantiomerically pure sulfonamide (R)-12. The desired product 16 can be prepared from (R)-12 following the steps described in Method 1.

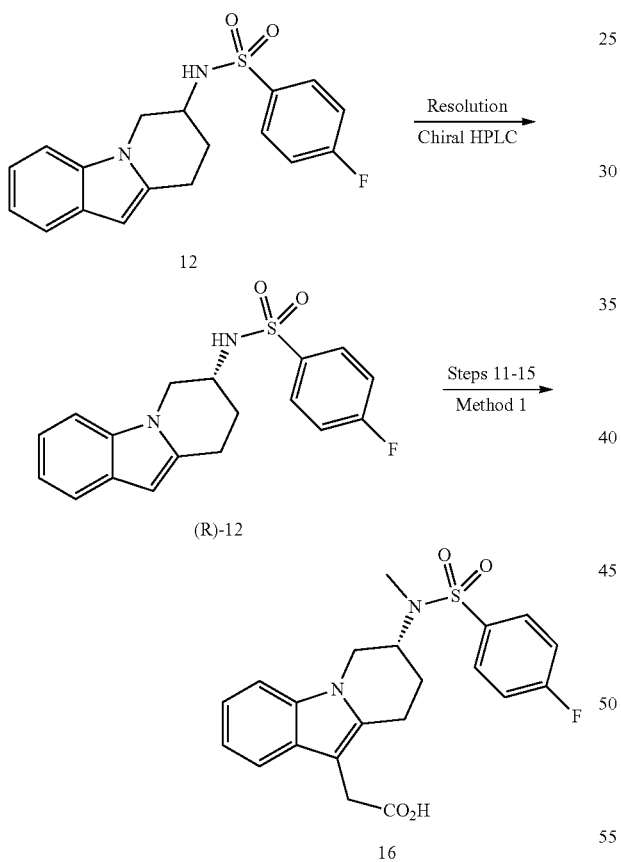

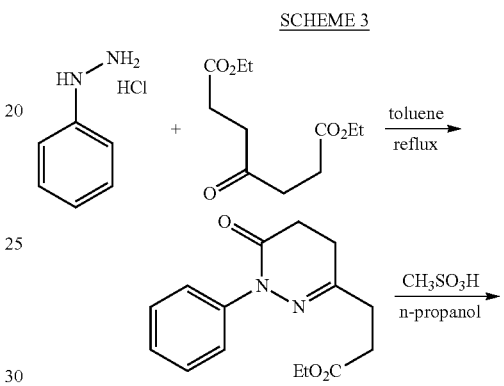

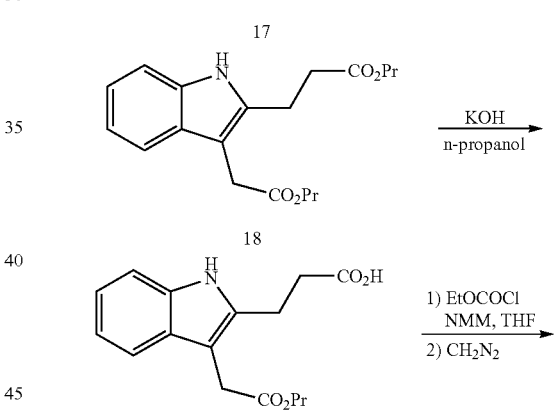

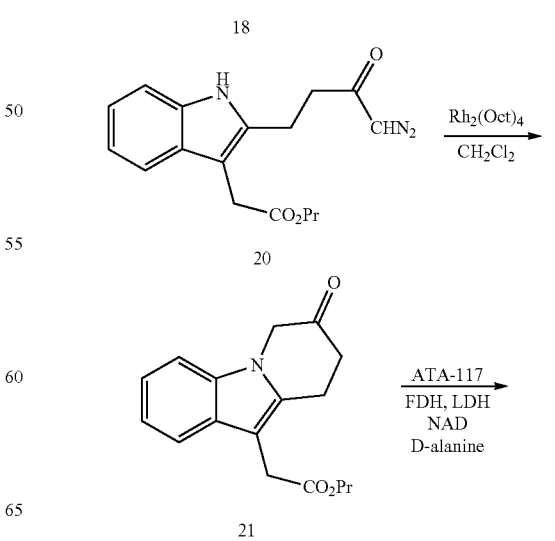

Method C (Scheme 3):

Dean-Stark condensation of phenyl hydrazine hydrochloride with diethyl 4-oxopimelate affords 17 which can be converted into indole 18 using an acid such as dry hydrogen chloride or methanesulfonic acid. Selective saponification of 18 with potassium hydroxide affords monoacid 19. Reaction of 19 with a chloroformate in the presence of a base such as -continued

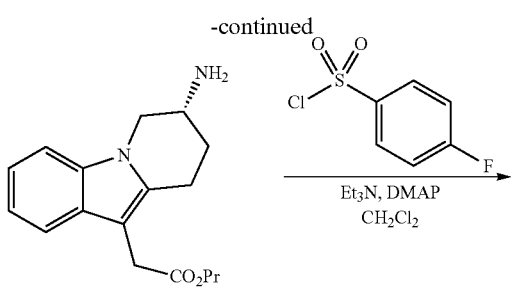

22

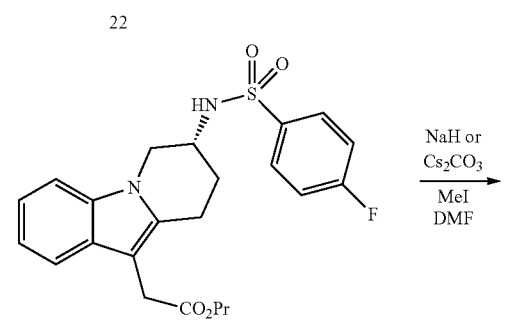

23

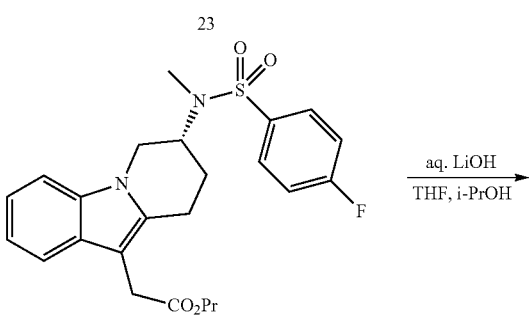

24

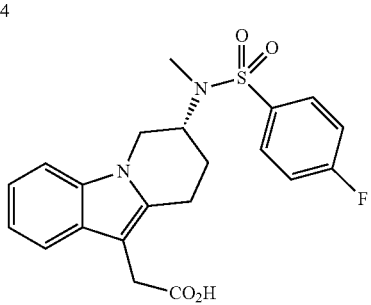

16

Method D (Scheme 4):

Esterification of D-Aspartic acid with thionyl chloride in methanol followed by treatment with 4-fluorophenylsulfonyl chloride affords the diester 25 which can be reduced with $NaBH_4$ to the corresponding diol 26. Aziridine formation can be accomplished via a Mistunobu variation of the Wenker synthesis by treating 26 with a phosphine and a 1,1'-azodicarbonyl compound to yield 27. Subsequent protection of the alcohol moiety with TBSCl gives the aziridine compound 28. Obviously, protecting groups other than a TBS ether that would be compatible with the following sequence of reactions could be employed instead. Indole acetic acid 29 can easily be esterified to the methyl ester 30. Treatment of 30 with a base such as sodium hydride followed by reaction with aziridine 28 and then methyl iodide affords 31. Removal of the silyl ether protecting group with fluoride anion gives the alcohol 32. Alternatively, 32 can be obtained directly from 30 if the crude 31 is treated with aqueous acid. Oxidation of the alcohol moiety can be accomplished by a Swern oxidation or with Dess-Martin periodinane and the resulting aldehyde can be subjected to an acid catalyzed cyclisation to give the unsaturated tricyclic indole 33. Hydrogenation of 33 provides 34 which upon saponification afford the desired indole acid 16.

SCHEME 4

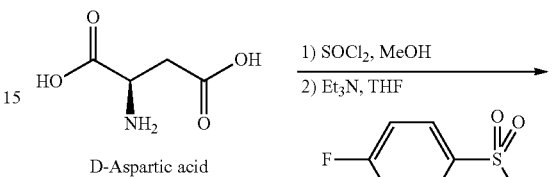

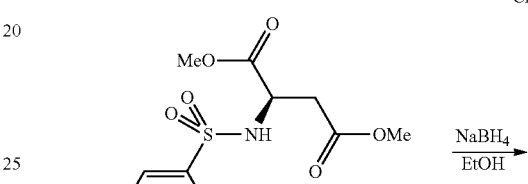

25

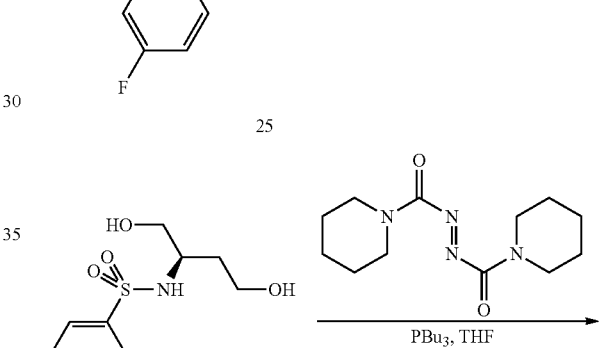

26

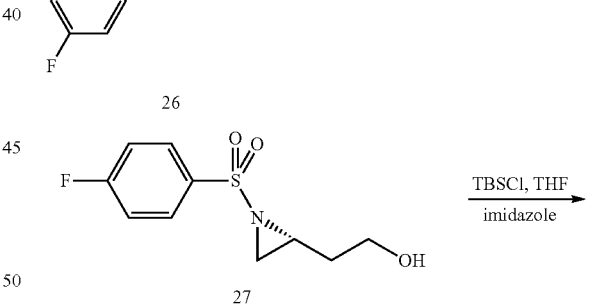

27

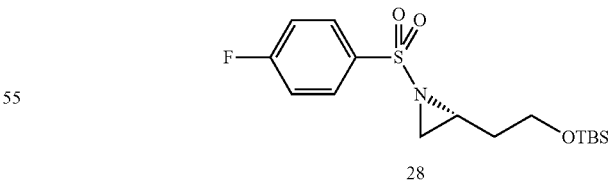

28

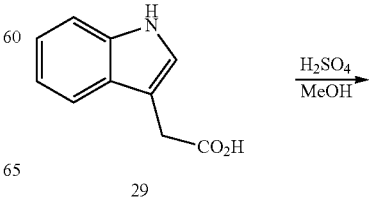

29

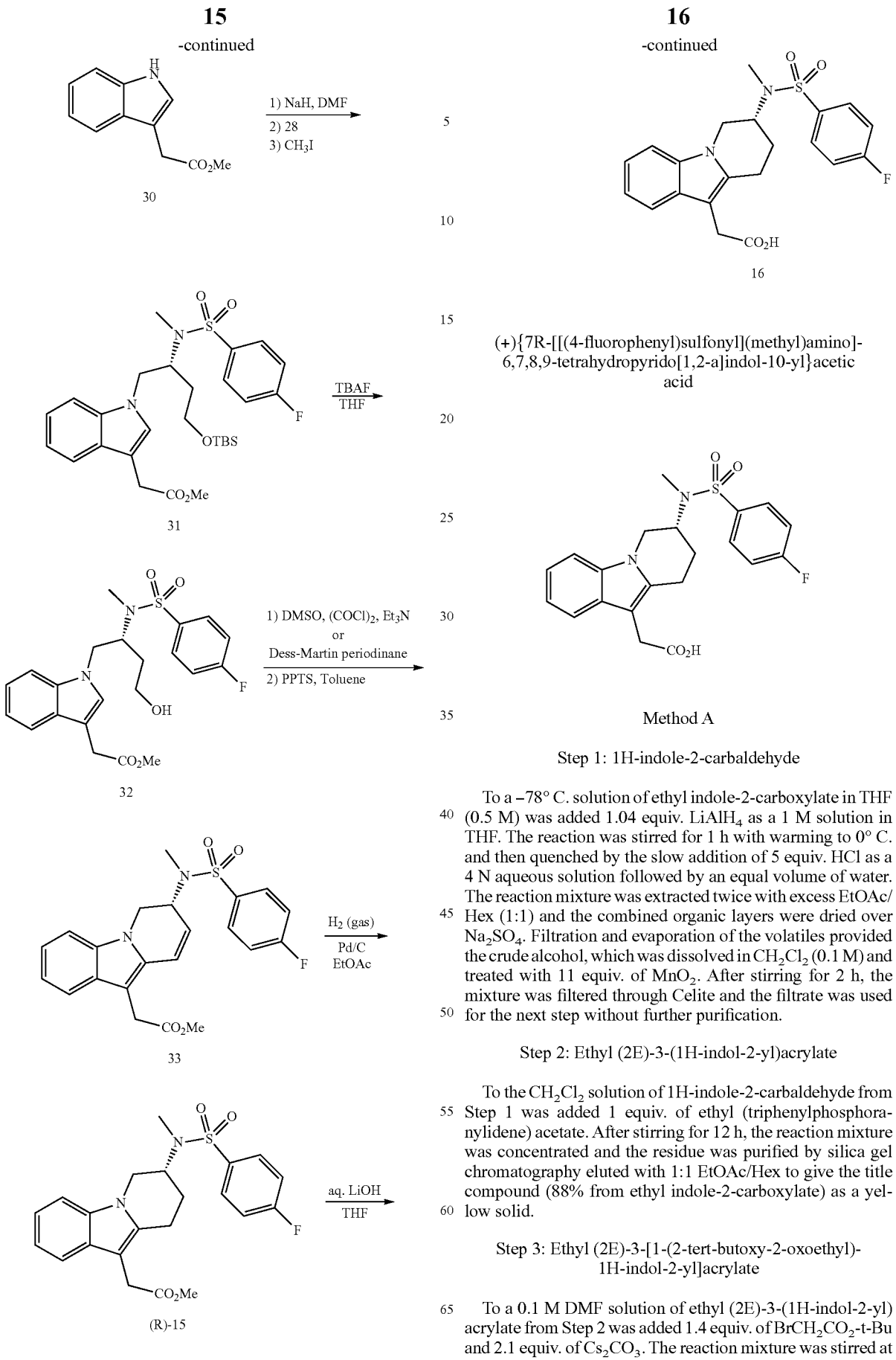

(+){7R-[[(4-fluorophenyl)sulfonyl](methyl)amino]-6,7,8,9-tetrahydropyrido[1,2-a]indol-10-yl}acetic acid Method A Step 1: 1H-indole-2-carbaldehyde To a −78° C. solution of ethyl indole-2-carboxylate in THF (0.5 M) was added 1.04 equiv. LiAlH$_4$ as a 1 M solution in THF. The reaction was stirred for 1 h with warming to 0° C. and then quenched by the slow addition of 5 equiv. HCl as a 4 N aqueous solution followed by an equal volume of water. The reaction mixture was extracted twice with excess EtOAc/Hex (1:1) and the combined organic layers were dried over Na$_2$SO$_4$. Filtration and evaporation of the volatiles provided the crude alcohol, which was dissolved in CH$_2$Cl$_2$ (0.1 M) and treated with 11 equiv. of MnO$_2$. After stirring for 2 h, the mixture was filtered through Celite and the filtrate was used for the next step without further purification.

Step 2: Ethyl (2E)-3-(1H-indol-2-yl)acrylate

To the CH$_2$Cl$_2$ solution of 1H-indole-2-carbaldehyde from Step 1 was added 1 equiv. of ethyl (triphenylphosphoranylidene) acetate. After stirring for 12 h, the reaction mixture was concentrated and the residue was purified by silica gel chromatography eluted with 1:1 EtOAc/Hex to give the title compound (88% from ethyl indole-2-carboxylate) as a yellow solid.

Step 3: Ethyl (2E)-3-[1-(2-tert-butoxy-2-oxoethyl)-1H-indol-2-yl]acrylate

To a 0.1 M DMF solution of ethyl (2E)-3-(1H-indol-2-yl) acrylate from Step 2 was added 1.4 equiv. of BrCH$_2$CO$_2$-t-Bu and 2.1 equiv. of Cs$_2$CO$_3$. The reaction mixture was stirred at 60° C. for 24 h, and was then diluted with an equal volume of acetone and filtered. The filtrate was concentrated and the residue was purified by silica gel chromatography eluted with EtOAc/Hex (1:2) to give the title compound (98%) as a syrup.

Step 4: Ethyl 3-[1-(2-tert-butoxy-2-oxoethyl)-1H-indol-2-yl]propanoate

To the ethyl (2E)-3-[1-(2-tert-butoxy-2-oxoethyl)-1H-indol-2-yl] acrylate from Step 3 in EtOAc (0.08 M) was added 10% palladium on carbon (50 mg per g of substrate). The reaction mixture was flushed a few times with hydrogen and then stirred overnight at rt under a 1 atmosphere pressure of hydrogen. The reaction mixture was diluted with $CH_2Cl_2$ (2 mL/g) and was filtered through Celite. The filtrate was concentrated to dryness to afford the title compound crude (100%) which was used in the next step without further purification.

Step 5: Tert-butyl 7-oxo-6,7,8,9-tetrahydropyrido[1,2-α]indole-6-carboxylate To a stirred solution of ethyl 3-[1-(2-tert-butoxy-2-oxoethyl)-1H-indol-2-yl]propanoate from Step 4 in THF (0.06 M) at −10° C. was added 1 M potassium tert-butoxide (2.5 equiv.) dropwise. The reaction mixture was allowed to warm to rt over a period of 1 h. and then stirred at rt overnight. The reaction mixture was poured into aqueous ammonium chloride and extracted with excess EtOAc (2×). The combined organic layers were washed with brine, dried with $MgSO_4$, filtered and concentrated under vacuum to afford the crude title compound (92%) as a dark oil. This material was used in the next step without further purification.

Step 6: 8,9-Dihydropyrido[1,2-α]indol-7(6H)-one

A solution of the crude tert-butyl 7-oxo-6,7,8,9-tetrahydropyrido[1,2-α]indole-6-carboxylate from Step 5 in toluene (0.06 M) was treated with silica gel (5 g per g of substrate) and the mixture was heated to reflux for 6 h. After cooling, the mixture was filtered, the cake washed with EtOAc and the combined organics were concentrated under vacuum to give the crude title compound (82%) as a brown solid. This material was used in the next step without further purification.

Step 7: (+/−) 6,7,8,9-Tetrahydropyrido[1,2-α]indol-7-ol

To a cooled (0° C.) solution of 8,9-dihydropyrido[1,2-α]indol-7(6H)-one from Step 6 in MeOH (0.3 M) was added $NaBH_4$ (1 equiv.) portionwise. After stirring for 1 h at 0° C., the reaction mixture was poured into an equal volume of saturated aqueous solution of $NH_4Cl$ and extracted (2×) with EtOAc. The combined organic layers were washed with brine, dried with $MgSO_4$ and concentrated under vacuum. The residue was purified by column chromatography on silica gel using a CombiFlashRF (Teledyne ISCO) eluting with EtOAc/Hex (10:90 to 60:40) to give the title compound (98%) as a yellow solid.

Step 8: (+/−) 7-Azido-6,7,8,9-tetrahydropyrido[1,2-α]indole

To a stirred solution of (+/−) 6,7,8,9-tetrahydropyrido[1,2-α]indol-7-ol from Step 7 in $CH_2Cl_2$ (0.2 M) at −40° C. was added triethylamine (1.2 equiv.) followed by methanesulfonyl chloride (1.1 equiv.). The reaction mixture was stirred at −40° C. for 30 min. and then was poured into aqueous sodium hydrogen carbonate and extracted with $CH_2Cl_2$ (2×). The combined organic layers were washed with brine, dried with $MgSO_4$ and concentrated under vacuum to afford the crude methanesulfonamide (91%) as a brown oil. This crude material was dissolved in DMF (0.2 M) and sodium azide (4.5 equiv.) was added. The reaction mixture was stirred at 60° C. overnight and then cooled to rt, poured into water and extracted with 1:1 EtOAc-Hex (2×). The combined organic layers were washed with water (2×), brine, dried with $MgSO_4$ and concentrated under vacuum. The residue was purified by short pad on silica gel eluting with EtOAc/Hex (10:90 to 30:70) to give the title compound (75%) as a light brown solid.

Step 9: (+/−) 6,7,8,9-Tetrahydropyrido[1,2-α]indol-7-amine

To a solution of (+/−) 7-azido-6,7,8,9-tetrahydropyrido[1,2-α]indole from Step 8 in MeOH (0.1 M) was added 10% palladium on carbon (200 mg per g of substrate). The reaction mixture was flushed a few times with hydrogen and stirred overnight at rt under a 1 atmosphere pressure of hydrogen. The reaction mixture was diluted with $CH_2Cl_2$ and was filtered through Celite, the cake was washed with EtOAc and the filtrate concentrated under vacuum. The residue was purified by column chromatography on silica gel eluting with $CH_2Cl_2$/MeOH/$NH_4OH$ (100:0:0 to 89:10:01) to give the title compound (81%) as a brown gum.

Step 10: (+/−) 4-Fluoro-N-(6,7,8,9-tetrahydropyrido[1,2-α]indol-7yl)benzenesulfonamide To a stirred solution of (+/−) 6,7,8,9-tetrahydropyrido[1,2-α]indol-7-amine from Step 9 in $CH_2Cl_2$ (0.14 M) at rt were added 4-fluorobenzenesulfonyl chloride (1.2 equiv.), triethylamine (5 equiv.) and DMAP (0.03 equiv). The reaction mixture was stirred at rt for 2 h. It was poured into aqueous $NaHCO_3$ and extracted with dichloromethane (2×). The combined organic layers were washed with brine, dried with $MgSO_4$ and concentrated under vacuum. The residue was purified by column chromatography on silica gel using using a CombiFlashRF (Teledyne ISCO) eluting with EtOAc/Hex (0:100 to 50:50 for 15 min, then at 50:50 for 5 min) to give the title compound (78%) as a light yellow foam.

Step 11: (+/−) 4-Fluoro-N-methyl-N-(6,7,8,9-tetrahydropyrido[1,2-α]indol-7-yl)benzene-sulfonamide To a 0° C. solution of (+/−) 4-fluoro-N-(6,7,8,9-tetrahydropyrido [1,2-α]indol-7-yl)-benzenesulfonamide from Step 10 in DMF (0.2 M) was added NaH (1.1 equiv.). The mixture was stirred for 30 min. Methyl iodide (1.25 equiv.) was added and the reaction was stirred for an additional 1 h at rt. The mixture was poured into aqueous $NH_4Cl$ and extracted with EtOAc (2×).

The combined organic layers were washed with water (2×), with brine, dried with $MgSO_4$ and concentrated under vacuum to afford the crude title compound (96%) as a yellow solid which was used in the next step without further purification. Pure compound can obtained following a swish from 2:1 Hex/EtOAc.

Step 12: (+/−) Methyl{7-[[(4-fluorophenyl)sulfonyl](methyl)amino]-6,7,8,9-tetrahydro-pyrido[1,2-α]indol-10-yl}(oxo)acetate To a 0° C. solution of (+/−) 4-fluoro-N-methyl-N-(6,7,8,9-tetrahydropyrido [1,2-α]indol-7-yl)benzenesulfonamide from Step 11 in CH$_2$Cl$_2$ (0.1 M) was added oxalyl chloride (2 equiv.) and the mixture was stirred for 1 h at 0° C. MeOH (20 equiv.) was added, the resulting mixture was stirred at rt for 1 h, and then poured into aqueous NaHCO$_3$ and extracted with CH$_2$Cl$_2$ (2×). The combined organic layers were washed with brine, dried with MgSO$_4$ and concentrated under vacuum to afford the crude title compound (100%) as a yellow solid. The material was used as such in the next step.

Step 13: (+/−) Methyl{7-[[(4-fluorophenyl)sulfonyl](methyl)amino]-6,7,8,9-tetrahydro-pyrido[1,2-α]indol-10-yl}(hydroxy)acetate To a stirred suspension of (+/−) methyl {7-[[(4-fluorophenyl)sulfonyl](methyl)amino]-6,7,8,9-tetrahydropyrido[1,2-α]indol-10-yl}(oxo)acetate from Step 12 in THF (0.1 M) at 0° C. was added NaBH$_4$ (1 equiv.) followed by MeOH (2.5 equiv.). The ice bath was removed and the reaction mixture was stirred at rt for 1 h. It was poured into aqueous NH$_4$Cl-1 N HCl and extracted with EtOAc (2×). The combined organic layers were washed with brine, dried with MgSO$_4$ and concentrated under vacuum. The residue was purified by column chromatography on silica gel using a CombiFlashRF (Teledyne ISCO) eluting with EtOAc/Hex (0:100 to 70:30) to afford the desired material (85%) as a foam.

Step 14: (+/−)Methyl{7[[(4-fluorophenyl)sulfonyl](methyl)amino]-6,7,8,9-tetrahydro-pridol[1,2-α]indol-10-yl}acetate To a stirred suspension of sodium iodide (7 equiv.) in acetonitrile (2 M) at rt was added TMSCl (7 equiv.) dropwise. The reaction mixture was stirred at rt for 15 min. A solution of (+/−) methyl {7-[[(4-fluorophenyl)sulfonyl](methyl)amino]-6,7,8,9-tetrahydropyrido[1,2-α]-indol-10-yl}(hydroxy)acetate from Step 13 in 1:1 Et$_2$O and acetonitrile was added (substrate final concentration=0.15 M), and the reaction mixture was stirred at rt for 30 min. It was poured into aqueous NaHCO$_3$ and aqueous Na$_2$S$_2$O$_3$ and extracted with EtOAc (2×). The combined organic layers were washed with brine, dried with MgSO$_4$ and concentrated under vacuum. The residue was purified by column chromatography on silica gel using a CombiFlashRF (Teledyne ISCO) eluting with EtOAc/Hex (0:100 to 40:60) to give the title compound (87%) as a light yellow foam.

Step 15: (+) {7R-[[(4-Fluorophenyl)sulfonyl](methyl)amino]-6,7,8,9-tetrahydropyrido[1,2-α]indol-10-yl}acetic acid The methyl (+/−){7-[[(4-fluorophenyl)sulfonyl](methyl)amino]-6,7,8,9-tetrahydropyrido[1,2-α]indol-10-yl}acetate obtained from Step 14 was resolved by chiral HPLC using a ChiralpakAD column and eluting with a mixture of 20% EtOH/20% /iPrOH/60% Hex to afford equal amounts of the fast eluting isomer (>99% ee) and of the slow eluting isomer (>99% ee). $^1$H NMR (400 MHz, acetone-d6) of the slow eluting isomer δ 8.10-8.05 (m, 2H), 7.51-7.40 (m, 3H), 7.26 (d, 1H), 7.14-7.01 (m, 2H), 4.58-4.48 (m, 1H), 4.19 (dd, 1H), 3.87 (t, 1H), 3.70-3.60 (m, 2H), 3.60 (s, 3H), 3.18-3.08 (m, 1H), 2.96 (s, 3H), 2.90-2.78 (m, 1H), 1.97-1.84 (m, 1H), 1.74-1.65 (m, 1H). The slow eluting isomer was dissolved in THF and MeOH (2:1, 0.07 M) at rt and aqueous 2 M LiOH was added (5 equiv.). The reaction mixture was stirred at rt for 2 h. It was poured into phosphate buffer pH 2 and extracted with EtOAc (2×). The combined organic layers were washed with brine, dried with MgSO$_4$ and concentrated under vacuum.

The residue was purified by column chromatography on silica gel eluting with EtOAc/Hex+acetic acid (50:50+1%) to give the title compound (100%) as a beige solid. $^1$H NMR (400 MHz, acetone-d6) δ 8.13-8.07 (m, 2H), 7.53-7.42 (m, 3H), 7.26 (d, 1H), 7.13-7.02 (m, 2H), 4.56-4.49 (m, 1H), 4.20 (dd, 1H), 3.96-3.86 (m, 1H), 3.69-3.57 (m, 2H), 3.20-3.10 (m, 1H), 2.98 (s, 3H), 2.90-2.72 (m, 1H), 2.00-1.89 (m, 1H), 1.75-1.68 (m, 1H). MS(-ESI): 414.7. Optical rotation $\alpha_D^{23}$: +62.0 (C=0.5, acetone).

Method B (+/−) 4-Fluoro-N-((7R)-6,7,8,9-tetrahydropyrido[1,2-α]indol-7-yl)benzenesulfonamide Racemic 4-fluoro-N-(6,7,8,9-tetrahydropyrido[1,2-α]indol-7-yl)benzene-sulfonamide from Method 1, Step 10 was resolved by chiral HPLC using a Chiralpak AD column and eluting with 30% MeOH/20% EtOH/ 20% i-PrOH/30% Hex with 0.25% Et$_3$N to afford equal amounts of the fast eluting isomer (>99% ee) and of the slow eluting isomer (>99% ee). $^1$H NMR (400 MHz, acetone-d6) of the slow eluting isomer δ 8.10-8.04 (m, 2H), 7.46-7.38 (m, 3H), 7.19 (d, 1H), 7.09-6.96 (m, 2H), 6.14 (s, 1H), 4.21 (dd, 1H), 4.01-3.93 (m, 1H), 3.83 (dd, 1H), 3.10-3.04 (m, 1H), 2.97-2.87 (m, 1H), 2.04-1.88 (m, 2H). This material was converted to (+){7R-[[(4-fluorophenyl)sulfonyl](methyl)amino]-6,7,8,9-tetrahydropyrido[1,2-α] indol-10-yl}acetic acid following Steps 11-15 from Method 1.

Method C

Step 1: Ethyl 3-(6-oxo-1-phenyl-1,4,5,6-tetrahydropyridazin-3-yl)propanoate

In a three neck flask equipped with a Dean-Stark trap, phenylhydrazine hydrochloride and diethyl 4-oxoheptanedioate (1 equiv.) were combined in Toluene (1.15 M). The suspension was stirred 48 h at reflux. The reaction mixture was cooled to rt and concentrated under vacuum to afford the desired material as a brown oil which was used as such in the next step.

Step 2: Propyl 3-[3-(2-oxo-2-propoxyethyl)-1H-indol-2-yl]propanoate

Methanesulfonic acid (1.15 equiv.) was added to a stirred solution of ethyl 3-(6-oxo-1-phenyl-1,4,5,6-tetrahydropyridazin-3-yl)propanoate from Step 1 in n-propanol (1.1 M). The mixture was stirred overnight at 80° C. The mixture was cooled to rt and neutralized with aqueous 1 N NaOH (1 equiv.). Final mixture was concentrated under vacuum, diluted with toluene and concentrated again. The residue was purified by column chromatography on silica gel using a CombiFlashRF (Teledyne ISCO) eluting with EtOAc/Hex (0:100 to 60:40) to give the title compound (79%) as a brown oil.

Step 3: 3-[3-(2-Oxo-2-propoxyethyl)-1H-indol-2-yl]propanoic acid

Aqueous 8 N KOH (1.05 equiv.) was added to a stirred solution of propyl 3-[3-(2-oxo-2-propoxyethyl)-1H-indol-2-yl]propanoate from Step 1 in n-propanol (0.5 M). The mixture was stirred at 50° C. for 4 h. The reaction mixture was cooled to rt, quenched with acetic acid (1.2 equiv.) and concentrated.

The residue was purified on a pad of silica gel using $CH_2Cl_2$, then $CH_2Cl_2$/EtOAc (9:1) and finally $CH_2Cl_2$/EtOAc/MeOH (88:10:2) to afford after evaporation of the volatiles, the desired material (68%) as yellow oil.

Step 4: Propyl [2-(4-diazo-3-oxobutyl)-1H-indol-3-yl]acetate

N-methylmorpholine (1.1 equiv.) was added dropwise over 1 h to a stirred, mixture of 3-[3-(2-oxo-2-propoxyethyl)-1H-indol-2-yl]propanoic acid from Step 3 and ethyl chloroformate (1.11 equiv.) in THF (0.4 M) cooled to 0° C. The reaction temperature was closely monitored during the addition and was not allowed to go over +2° C. The mixture was stirred at 0° C. an additional 30 min. A white precipitate formed rapidly. Diazomethane (0.3 M in $Et_2O$, 1.8 equiv.) was added and the final mixture was stirred for 2 h at 0° C. The mixture was filtered and the supernatant was concentrated under vacuum (with AcOH put in the vacuum trap to quench excess diazomethane). The residue was purified by column chromatography on silica gel using a CombiFlashRF (Teledyne ISCO) eluting with EtOAc/Hex (10:90 to 60:40) to give the title compound (63%) as a yellow solid.

Step 5: Propyl (7-oxo-6,7,8,9-tetrahydropyrido[1,2-α]indol-10-yl)acetate

Rhodium (II) octanoate dimer (0.1 equiv.) was added to a $CH_2Cl_2$ solution (0.02 M) of propyl [2-(4-diazo-3-oxobutyl)-1H-indol-3-yl]acetate from Step 4. The reaction mixture was stirred overnight at rt and then concentrated. The residue was purified by column chromatography on silica gel using a CombiFlashRF (Teledyne ISCO) eluting with EtOAc/Hex (2:98 to 10:90) to give the title compound (64%) as a yellow solid.

Step 6: Propyl ([7R]-7-amino-6,7,8,9-tetrahydropyrido[1,2-α]indol-10-yl)acetate

Sodium phosphate, dibasic (3.8 equiv.) and sodium formate (266 equiv.) were added to a solution of D-Alanine (38 equiv.) in water. The pH was measured as 7.6. Nicotinamide Adenine Dinucleotide (0.04 equiv.), Pyridoxal-5-phosphate (0.11 equiv.), Lactate dehydrogenase (1 equiv.), Formate dehydrogenase (1 equiv.), and Amine-Transaminase-117 (1 equiv.) were added under stirring and slowly dissolved. The measured pH was 7.3. The mixture was aged at 22° C. for 1 h. The flask was flushed with nitrogen and propyl (7-oxo-6,7,8,9-tetrahydropyrido[1,2-α]indol-10-yl)acetate from Step 5 was added as a DMSO (0.06 M) solution. The reaction was adjusted to pH 7.2 and aged at 30° C. overnight under nitrogen atmosphere. Upon completion of the reaction as determined by HPLC, the pH of the reaction was adjusted to pH 4.0 with 6 N HCl and Celite (20 g per L) was added. After stirring for 1 hr the reaction was filtered through a Celite bed and the filter cake was washed twice with 0.1 N HCl. The combined aqueous filtrate was extracted with 1 volume of MTBE. The organic layer did not contain amine and was discarded. The aqueous layer was diluted with an equal volume of MTBE and the pH of the mixture was adjusted to pH 9.5 using 5N NaOH. The two phases were separated and the aqueous layer was extracted with MTBE. The spent aqueous layer had no detectable amine and was discarded. The combined organic layers were washed with dilute sodium carbonate and dried over $Na_2SO_4$. Evaporation of the volatiles afforded the crude title compound (80%). The ee was determined as 99% by SFC assay. The SFC conditions are ADH column (250×4.6 mm, 5 um), isocratic 20% MeOH, 25 mM iso-proply amine/CO2, 2 ml/min, 35° C., 200 bar, 215 nm, 15 min. Under these conditions the desired R-amine has an 8.99 min retention time (S-amine; 5.82 min)

Step 7: Propyl {(7R)-7-{[(4-fluorophenyl)sulfonyl]amino}-6,7,8,9-tetrahydropyrido[1,2-α]indol-10-yl}acetate To a $CH_2Cl_2$ solution (0.2 M) of propyl ([7R]-7-amino-6,7,8,9-tetrahydro-pyrido[1,2-α]indol-10-yl)acetate from Step 6 was added 4-fluorobenzenesulfonyl chloride (1.1 equiv.) followed by triethylamine (3 equiv.) and DMAP (1 equiv.). The reaction mixture was stirred for 12 h at rt. The mixture was concentrated under reduced pressure, diluted with EtOAc, and washed with aqueous $NaHCO_3$, water and finally with brine. The organic layer was dried with $Na_2SO_4$, filtered and concentrated. The residue was purified by column chromatography on silica gel using a CombiFlashRF (Teledyne ISCO) eluting with EtOAc/Hex (10:90 to 50:50) to give the title compound (97%) as a colorless foam.

Step 8: Propyl {(7R)-7-{[(4-fluorophenyl)sulfonyl](methyl)amino}-6,7,8,9-tetrahydro-pyrido[1,2-α]indol-10-yl}acetate Sodium hydride (1.05 equiv.) was added to a 0° C. DMF solution (0.14 M) of propyl {(7R)-7-{[(4-fluorophenyl)sulfonyl]amino}-6,7,8,9-tetrahydropyrido [1,2-α]indol-10-yl}acetate from Step 7 and the mixture was stirred at 0 ° C. for 30 min. Iodomethane (3 equiv.) was added and the reaction was stirred at 0° C. for 2 h. The mixture was poured in aqueous $NH_4Cl$ and extracted with $Et_2O$ (2x). The combined organic extracts were washed with water (3x), brine and then dried with $MgSO_4$, filtered and concentrated under vacuum. The residue was purified by column chromatography on silica gel using a CombiFlashRF (Teledyne ISCO) eluting with EtOAc/Hex (5:95 to 50:50) to give the title compound (98%) as a colorless oil.

Step 9: (+) {7R-[[(4Fluorophenyl)sulfonyl](methyl)amino]-6,7,8,9-tetrahydropyrido [1,2-α]indol-10-yl}acetic acid The propyl {(7R)-7-{[(4-fluorophenyl)sulfonyl](methyl)amino}-6,7,8,9-tetrahydropyrido[1,2-α]indol-10-yl}acetate from Step 8 was dissolved in a 2:1 mixture of iso-propanol and THF (0.06 M). Aqueous 1 N LiOH (3 equiv.) was added and the mixture was stirred overnight at rt. The mixture was concentrated under vacuum, poured in 1 N HCl and extracted (2x) with EtOAc. The combined organic layers were washed with water, brine and then dried with $MgSO_4$, filtered and concentrated under vacuum to give the title compound (96%). The material was recrystallized in refluxing EtOAc to afford after filtration and drying under air flow the desired material 99.7% pure by HPLC. The enantiomeric excess (ee) was determined by preparing a small amount the corresponding methyl ester using diazomethane and analyzing it as described in Method A, Step 15. The ee was found to be 99% which indicate that no racemization took place during the last three steps of the sequence from the chiral amine of Step 6.

Method D

Step 1: Dimethyl (2R)-2-{[(4-fluorophenyl)sulfonyl]amino}succinate

To a mixture of dimethyl aspartate—HCl salt (1 equiv) and 4-F-benzenesulfonyl chloride (1.1 equiv) in THF (4 ml/g) was added triethylamine (3.1 equiv) was added and the reaction was stirred overnight. The suspension was filtered and quenched with 1 M HCl. The layers were cut and the aqueous layer was back extracted with MTBE. The combined organic phases were washed with brine, dried over MgSO₄ and concentrated in vacuo to provide the desired material (93%) as a light yellow oil.

Step 2: 4-Fluoro-N-[(1R)-3-hydroxy-1-(hydroxymethyl)propyl]benzenesulfonamide

To a cooled (0° C.) solution of dimethyl (2R)-2-{[(4-fluorophenyl)sulfonyl]-amino}succinate (1 equiv.) from step 1 in EtOH (10 mL/g) was added NaBH₄ (5 equiv.) in 3 portions and the reaction was stirred overnight at rt. The reaction was quenched with brine (5 mL/g) and filtered. The solid was suspended in EtOAc (10 mL/g). The mother liquor was concentrated in vacuo and then saturated with NaCl. The EtOAc suspension was then filtered.

The mother liquor from this filtration was used to extract the aqueous layer. The aqueous layer was extracted twice with EtOAc. The combined organics were washed with brine, dried over MgSO₄ and concentrated in vacuo. The crude product was dissolved in acetone (5 mL/g) to crash out any boron salts and filtered over solkafloc to afford after evaporation the desired material (60%).

Step 3: 2-{(2R)-1-[(4-fluorophenyl)sulfonyl]aziridin-2-yl}ethanol

To a solution of 4-fluoro-N-[(1R)-3-hydroxy-1-(hydroxymethyl)propyl]benzene-sulfonamide (1 equiv) from step 2 in THF (20 mL/g) was added azodicarboxylic acid dipiperidide (1 equiv) followed by tri-n-butylphosphine (1 equiv) dropwise over 30 min. The reaction was stirred for 30 min then filtered. The filtrate was washed with THF and H₂O (5 mL/g), then added to the resulting solution and stirred for 1 h. NaCl was added to separate the aqueous and organic layers. The layers were cut and the organic layer washed with brine, dried over MgSO₄ and concentrated in vacuo. The crude product was triturated in MTBE and filtered. The resulting solution was concentrated and triturated in EtOAc/Hex (1:1) and then filtered. The resulting solution was then concentrated and purified by column chromatography with EtOAc/Hex 25-75% to give the desired material (77%) as a light yellow oil.

Step 4: (2R)-2-(2-{[tert-butyl(dimethyl)silyl]oxy}ethyl)-1-[(4-fluorophenyl)sulfonyl]-aziridine To the 2-{(2R)-1-[(4-fluorophenyl)sulfonyl]aziridin-2-yl}ethanol from Step 3 dissolved in THF (0.2 M) was added TBSCl (1.1 equiv.) followed by imidazole (2.2 equiv.). The reaction mixture was stirred 1 h at rt, then filtered with washing of the solids with MTBE. The combined organics were washed (2×) with 1M HCl, brine (2×), dried over MgSO₄, filtered and concentrated in vacuo. The residue was purified by column chromatography eluting with EtOAc/Hex (1:9) to give the title compound (85%) as a white solid.

Step 5: Methyl 1H-indol-3-ylacetate

Concentrated sulfuric acid (0.2 equiv.) was carefully added to a solution of 1H-indol-3-ylacetic acid in MeOH (1 M) and the reaction was stirred at rt for 2.5 h. The solution was cooled with an ice bath, and aqueous 2 N NaOH (0.18 equiv.) was slowly added such that T<10° C. The solution was diluted with water, and solid K₂CO₃ was then added until pH was neutral. The solution was extracted with MTBE (2×), washed with water (2×), brine, dried over Na₂SO₄, filtered, and concentrated to give a brown syrup. The crude syrup was dissolved in MTBE (1.4 mL/g) and transferred to a three necked flask fitted with a temperature probe, mechanical stirrer, addition funnel and nitrogen inlet. Hex was then slowly added to the stirring solution over 1 h. More Hex was then added over 2 h then left overnight. The suspension was filtered, washed with Hex, and dried on the fit under nitrogen for 20 h to give the title compound (81%) as a light orange solid.

Step 6: Methyl (1-{(2R)-2-[[(4-fluorophenyl)sulfonyl](methyl)amino]-4-hydroxybutyl}-1H-indol-3-yl)acetate A three necked round bottom flask fitted with a magnetic stir bar, nitrogen inlet, temperature probe and addition funnel was charged with sodium hydride (2 equiv.) and DMF. The mixture was cooled to 0° C., and a solution of methyl 1H-indol-3-ylacetate (2 equiv.) from Step 5 in DMF (1 M) was added dropwise. After the addition, the reaction was stirred for 15 min, upon which a DMF (0.5 M) solution of (2R)-2-(2-{[tert-butyl(dimethyl)silyl]oxy}ethyl)-1-[(4-fluorophenyl)sulfonyl]aziridine (1 equiv.) from Step 4 was added dropwise. The reaction was allowed to stir 1.5 h. Methyl iodide (5 equiv.) was then added to the reaction and stirred an additional 1 h. Aqueous 2M HCl (7.2 equiv.) was then added carefully to the reaction followed by an equal volume of EtOAc and stirring continued for 2 h. The solution was diluted with EtOAc and layers separated. The organic phase was washed with ½ saturated brine (2×), dried over Na₂SO₄, filtered and concentrated to an orange syrup. The syrup was diluted with MTBE upon which solid started to form. The suspension was vigorously stirred while additional MTBE was added dropwise over 15 min. The suspension was cooled to 0° C. and Heptanes was added dropwise. The reaction was stirred for 1 h, and filtered. The solid cake was washed with MTBE/Heptanes (2:1) and dried on the fit under nitrogen for 16 h to provide the title compound (75%) as a white solid.

Step 7: Methyl {(7 R)-7 -[[(4-fluorophenyl)sulfonyl](methyl)amino]-6,7-dihydro pyrido[1,2-α]indol-10-yl}acetate A solution of CH₂Cl₂, oxalyl chloride (0.54 M, 1.2 equiv.) was cooled to −76° C. DMSO (2.5 equiv.) was then added dropwise such that T<−60 ° C. The mixture was stirred for 30 min, upon which methyl (1-{(2R)-2-[[(4-fluorophenyl)sulfonyl](methyl)amino]-4-hydroxy-butyl}-1H-indol-3-yl)acetate from Step 6 was added as a solution in CH₂Cl₂ (0.3 M). The reaction was stirred an additional 30 min. Triethylamine (4 equiv.) was then added dropwise, and the reaction warmed to rt and stirred for 2 h. The reaction was quenched by the addition of saturated NaHCO₃. The layers were separated, and the aqueous back-extracted with CH₂Cl₂ (2×). The combined organic phases were washed with brine, dried over Na₂SO₄, filtered through a plug of SiO₂ and concentrated to give a yellow foam. This crude aldehyde was dissolved in toluene (0.25 M) and charged in a three necked round bottom flask fitted with a temperature probe, nitrogen inlet, reflux condenser, and mechanical stirrer. Pyridinium p-toluenesulfonate (0.2 equiv.) was added, and the reaction heated to 60° C. for 16 h (protected from light with aluminum foil). The reaction was diluted with water and extracted with EtOAc. The layers were separated, and the aqueous back extracted with EtOAc. The combined organics were washed with brine, dried over Na₂SO₄, filtered, concentrated and the residue was purified by column chromatography on silica gel using automatized gradiant pump system CombiFlashRF (Teledyne ISCO) eluting with EtOAc/Hex (20:80 to 40:60) to give a light yellow foam. This light yellow foam was then swished by dissolving in EtOAc (2 mL/g), slow addition of MTBE (5 mL/g), then slow addition of Heptanes (7 mL/g) to give the title compound (73%) as an off white solid . The mother liquor was concentrated and purified by flash again to more (7%) of the desired compound.

Step 8: Methyl {(7R)-7-[[(4-fluorophenyl)sulfonyl](methyl)amino]-6,7,8,9-tetrahydro-pyrido[1,2-α]indol-10-yl}acetate To a solution of methyl {(7R)-7-[[(4-fluorophenyl)sulfonyl](methyeamino]-6,7-dihydropyrido[1,2-α]indol-10-yl}acetate (1 equiv.) from step 7 in EtOAc (0.25 M) was added 10% Pd-C (20 mg/mmol) and the flask thoroughly purged with nitrogen. The stirring black solution was purged with hydrogen gas, then left under 1 atmosphere pressure of hydrogen and protected from light. The reaction was stirred for 24 h and then filtered through a plug of Celite 545, the plug was washed with EtOAc (2×), and the combined organics were concentrated under vacuum to give a yellow foam. Purification by column chromatography on silica gel using a CombiFlashRF (Teledyne ISCO) eluting with EtOAc/Hex (20:80 to 40:60) gave the title compound (91%) as a light yellow foam.

Step 9: (+) {7R-[[(4-fluorophenyl)sulfonyl](methyl)amino]-6,7,8,9-tetrahydropyrido[1,2-α] indol-10-yl}acetic acid Freshly prepared 1N LiOH (3 equiv.) was slowly added dropwise to a solution of methyl {(7R)-7-[[(4-fluorophenyl)sulfonyl](methyl)amino]-6,7,8,9-tetrahydropyrido[1,2-α]indol-10-yl}acetate from Step 8 in THF (0.45 M). The reaction solution was stirred at rt for 16 h and aqueous 1M HCl (10 equiv.) was then added dropwise over 1 h at rt. The light green precipitate was filtered, rinsed with 1M HCl and dried for 48 h to give a light green powder. This material was suspended in EtOAc (2 ml/g) and vigorously stirred. At rt, MTBE (2 mL/g) was added dropwise over 1 h. The suspension was stirred for 2 h, upon which Heptanes (6 ml/g) was added slowly over 2 h. The suspension was stirred an additional 2h, then was filtered to provide the title compound (96%) as a pale off-white solid. See characterization in Method A, Step 15.

Biological Assays

Radioligand binding assay: Radioligand binding assays were performed at rt in 10 mM HEPES/KOH pH 7.4, 1 mM EDTA containing 10 mM $MnCl_2$ and 0.7 nM [$^3$H]$PGD_2$ (NEN, 171 Ci mmol$^{-1}$), in a final volume of 0.2 ml. Competing ligands were diluted in dimethyl-sulfoxide ($Me_2SO$) that was kept constant at 1% (v/v) of the final incubation volume. The reaction was initiated by the addition of 8-20 μg of membrane protein prepared from a HEK-hCRTH2 cell line. Total and non-specific binding were determined in the absence and the presence of 10 μM $PGD_2$, respectively. Under these conditions, specific binding (total minus non-specific) of the radioligand to the receptor reached equilibrium within 50 min and was stable up to 180 min. The reaction was routinely conducted for 60 min at rt and terminated by rapid filtration through prewetted Unifilters GF/C (Packard), using a Tomtec MachIII semi-automated harvester (for HEK-hCRTH2). The filters were then washed with 4ml of the same buffer and residual radioligand bound to the filter was determined by liquid scintillation counting following equilibration in 25 μL Ultima Gold F™(Unifilter) (Packard). In this assay, Compound A showed Ki of 2.5 nM.

i[cAMP] measurements: HEK-hCRTH2 cells were grown to 80-90% confluency. On the day of the assay, the cells were washed with PBS, incubated for 2 min in cell dissociation buffer, harvested by centrifugation at 300 g for 5 min at rt and re-suspended at 1.25e10$^6$ cells ml$^{-1}$ in Hanks' balanced salt solution containing 20 mM HEPES pH 7.4 and 0.75 mM IBMX (HBSS/HEPES/IBMX). The assay was performed in 384-plate format with 0.01 ml HBSS/HEPES/IBMX per well containing 12 500 cells and 75 nl of the test compound at various concentrations. Following a 10 min pre-incubation of the cells with the test compound at 37° C., 0.005 mL of Forskolin/DK-$PGD_2$ dilute in HBSS 20 mM Hepes, was added at a respectively final concentration of 10 uM and 150 nM, to initiate the reaction. After 10 min incubation at 37° ° C., the cAMP content was quantified using the cAMP XS+HitHunter chemiluminescence assay. (GE Healthcare 90-0075). % inhibition was calculated using the Forskolin and EC85 DK-PGD2 controls.

Eosinophil shape change assay in human whole blood: Blood was collected in vacutainers containing EDTA. The antagonist was added to blood and incubated for 10 min at rt. DK-$PGD_2$ (13,14-dihydro-15-keto prostaglandin $D_2$) was then added to blood for 4 min at 37° C. in a running water bath. Blood cells were then fixed in presence of cold 0.25% (v/v) paraformaldehyde prepared in 75% (v/v) PBS for 1 min on ice. 175 μL of fixed blood was transferred into 870 μL of cold 155 mM $NH_4Cl$ lysis solution and incubated at 4° C. for at least 40 min. The solution was then centrifuged at 430 g for 5min and the supernatant was discarded. Centrifuged cells were analyzed with a FACs Calibur flow cytometer (Becton Dickinson). Flow cytometry raw data were analyzed with FlowJo software by isolating the eosinophils from the neutrophils based on their high autofluorescence and determining the percent of total eosinophils with increased FSC-H value. Maximum (100%) and minimum (0%) shape change were determined in the presence of 10 μM DK-$PGD_2$ and PBS, respectively. A dose response curve with DK-$PGD_2$ was performed with every assay to determine the $EC_{50}$ for each blood donor.

Compounds were tested in 10-dose titration curves in the presence of 30 nM DK-$PGD_2$ to determine an antagonist $IC_{50}$.

Compound A is selective for the CRTH2 receptor over the DP and other prostanoid receptors. Assays on the DP, as well as other prostanoid, receptors are described in WO2003/06220.

What is claimed is:
1. The compound (+) {7R-[[(4-fluorophenyl)sulfonyl](methyl)amino]-6,7,8,9-tetrahydropyrido[1,2-α]indol-10-yl}acetic acid or a pharmaceutically acceptable salt thereof.
2. A pharmaceutical composition comprising a therapeutically effective amount of the compound of claim 1 or a pharmaceutically acceptable salt thereof and a pharmaceutically acceptable carrier.

* * * * *